United States Patent [19]

Perkins et al.

[11] Patent Number: 5,243,297

[45] Date of Patent: Sep. 7, 1993

[54] ELECTRICAL RESISTANCE TEMPERATURE COMPENSATED CORROSION PROBE WITH INDEPENDENT TEMPERATURE MEASUREMENT

[75] Inventors: Allan J. Perkins, La Habra; David K. Waterman, Santa Fe Springs; Albert L. Cheser, Anaheim, all of Calif.

[73] Assignee: Rohrback Cosasco Systems, Inc., Santa Fe Springs, Calif.

[21] Appl. No.: 872,499

[22] Filed: Apr. 23, 1992

[51] Int. Cl.$^5$ .................. G01R 27/02; G01N 17/04
[52] U.S. Cl. ............................. 324/700; 324/71.2; 324/691; 324/721; 204/153.11; 204/404
[58] Field of Search ............... 324/691, 700, 705, 721, 324/71.1, 71.2; 427/10; 204/404, 153.11

[56] References Cited

U.S. PATENT DOCUMENTS

| | | | |
|---|---|---|---|
| 3,609,549 | 9/1971 | Hausler et al. | 324/700 |
| 4,217,544 | 8/1980 | Schmidt | 324/721 |
| 4,338,563 | 7/1982 | Rhodes et al. | 324/700 |
| 4,436,438 | 3/1984 | Voznick | 374/165 |
| 4,514,681 | 4/1985 | Finley et al. | 324/65 |
| 4,587,479 | 5/1986 | Rhoades et al. | 324/65 |
| 4,755,744 | 7/1988 | Moore et al. | 324/65 |
| 4,839,580 | 6/1989 | Moore et al. | 324/65 |
| 4,882,537 | 11/1989 | Silverman | 324/65 |

Primary Examiner—Gerard R. Strecker
Assistant Examiner—Diep Do
Attorney, Agent, or Firm—Poms, Smith, Lande & Rose

[57] ABSTRACT

An electrical resistance corrosion probe incorporates a temperature sensitive resistor (RTD) that directly measures temperature of the probe and therefore of its environment as corrosion measurements are being made. The temperature sensitive resistor has one end connected to the common junction between the test and reference elements of the corrosion probe and has its other end connected in the common line to the several corrosion measuring circuits, including the test, reference and check circuits.

28 Claims, 4 Drawing Sheets

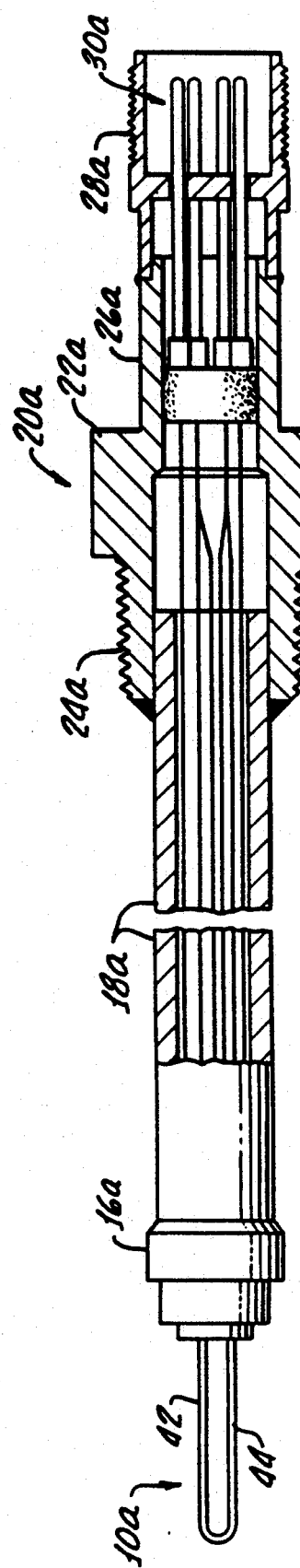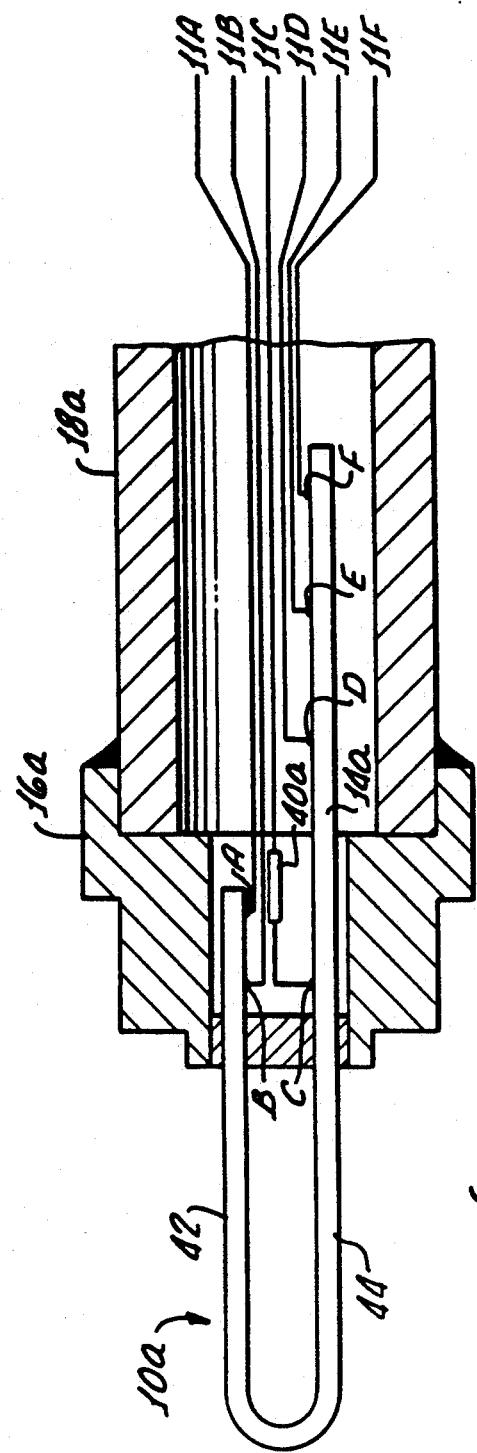

ELECTRICAL RESISTANCE TEMPERATURE COMPENSATED CORROSION PROBE WITH INDEPENDENT TEMPERATURE MEASUREMENT

BACKGROUND OF THE INVENTION

The present invention relates to temperature measurement and more particularly concerns integration of temperature measurement in an electrical resistance corrosion measuring probe.

DESCRIPTION OF PRIOR ART

A common method of continuous measurement of corrosion characteristics, frequently used for various types of fluid systems, such as oil refining processes, for example, employs resistance measurement of a metallic corrodible or erodible test element to indicate by change of resistance the amount of metal that has been lost by corrosion or erosion over a period of time. A widely used sensor for this measurement is known under the registered trademark CORROSOMETER manufactured Rohrback Cosasco Systems, Inc., assignee of the present application. One such sensor employs a tubular metallic test loop or wire, part of which operates as a reference element, made of the same material as the test element. The reference element is protected from the environment while the test element is exposed to the environment. Current is passed through the elements, and electrical resistance of each is measured while or after the sensor has been immersed in an environment of which corrosive tendencies are to be monitored. Because resistance varies with the amount of metal in the test element, measurement of test element resistance provides an indication of metal loss and, therefore, of corrosion or erosion. However, because resistance of the metal also changes with temperature, a reference element is provided, made of the same material as the test element, and having the same temperature resistance characteristics. Therefore, changes in resistance of the test element that are due to long term, relatively slow temperature variations may be eliminated by comparison (e.g. determining the ratio) of resistances of the test and reference elements. Other physical configurations of electrical resistance probes include a cylindrical metallic test element carrying an inner concentric reference element made of the same material as the test element, with the interior of the test element filled with a thermally conductive electrically non-conductive compound, thereby providing physical support for the preferably very thin wall of the test element.

In the measurement of corrosion it is often necessary to know the temperature of the environment being measured. Knowledge of this temperature is also useful independently of any corrosion measurement. Nevertheless, for improved evaluation of actual corrosion rates and corrosion conditions, as indicated by the conventional corrosion probe, knowledge of the temperature of the corrosive environment adjacent the probe is significant. In many processes corrosion rate varies with temperature so that it is necessary to know the temperature at which a corrosion reading is made. For example, in a fractionation tower different components of the material are extracted at different locations and at different temperatures. Therefore measurement of temperature of each component provides more useful information concerning the measured corrosion at the different locations. Knowledge of temperature at which a corrosive measurement is made is particularly useful in the measurement of corrosive characteristics of vapor in an above ground tank that stores petroleum products or other chemicals. Temperature, and therefore corrosive tendencies, of such corrosive vapors is more likely to fluctuate significantly because of the high thermal transmissivity of the vapor and the exposure of the tank to the variable outside environment. These are only some of the many different advantages of incorporating a temperature measurement with a corrosion measurement.

U.S. Pat. Nos. 4,338,563 for Corrosion Measurement with Secondary Temperature Compensation and 4,587,479 for Corrosion Measurement with Multiple Compensation describe systems employing thermocouples that measure temperatures of each of the test and reference elements and employ the difference in such temperatures to provide a short-term secondary temperature compensation of a corrosion probe. However, in certain types of probes, particularly in probes of the type mentioned above known as the CORROSOMETER, it is not feasible to employ thermocouple temperature sensing within the probe without using thermocouple extension cables and additional pins for the probe connector, or, alternatively, seriously compromising the data due to errors caused by varying and spurious thermocouple signals and lengths of cable to which the probe may be connected.

A typical probe, such as the CORROSOMETER mentioned above, embodies a probe body incorporating the test and reference elements and having a six pin connector part by which it is detachably connected to measuring instrumentation. Each of the six pins of this connector part is coupled to an individual connection point within the probe body. The connector part itself is coupled by a standard six pin connector part to a length of standard cable, which itself is connected to the various energizing and measuring circuits. This six pin connector system is widely used at present. Any change from the standard six pin connector and cable would be inconvenient and costly. Yet, use of thermocouples may require additional pins and cable wires. Moreover, to employ thermocouples within the probe requires the use of wires of different materials to create the thermocouple junctions, and such wires must be connected at their multi-pin connector ends to standard copper wires. This introduces additional thermocouples to the circuitry which makes reliable and repeated precision measurement difficult or not feasible in a standard commercial instrument. If additional separate leads (of thermocouple material) are employed for defining the thermocouple junctions without introducing additional thermocouple junctions, the instrument can no longer use a standard six pin connector, and thus may not be compatible with existing instrumentation or connecting cables.

Use of resistance temperature devices or resistance temperature detectors (RTD), which are temperature sensitive resistors (platinum is commonly used) has been suggested, but the relatively high resistance of such resistors as compared to the resistance of the test and reference elements of the corrosion probe has been found to greatly distort sensitive resistance measurements. Resistances of test and reference elements of typical electrical resistance corrosion probes are established in the order of milli ohms, whereas a common small size platinum temperature sensitive resistor has a nominal resistance of about 100 ohms, some one hundred thousand times greater. The effect of the temperature sensitive resistor is to overwhelm the measurement of the small test and reference element resistances.

Accordingly, it is an object of the present invention to provide a combined corrosion and temperature sensing probe that avoids or minimizes above-mentioned problems.

SUMMARY OF THE INVENTION

In carrying out principles of the present invention in accordance with a preferred embodiment thereof an electrical resistance probe includes a test element having a test connection point, a reference element having a reference connection point and connected to the test element at a common connection point. Measuring circuits have inputs connected to the test and reference connection points and also have a common input. A temperature sensitive resistor is connected between the common input of the measuring circuits and the common connection point. Connection of the relatively high resistance temperature sensitive resistor in common to both the test and measuring circuits offsets the gains of the test and reference amplifiers equally, which compensates for the effect of the large resistance temperature sensitive resistor, which thereby does not adversely affect the corrosion measurement. Effect of the temperature sensitive resistor on the corrosion measurement is eliminated because the measurement is made by comparing (determining the ratio of) the test resistance with the reference resistance.

Single conductive wires are connected from elements within the probe to the pins of a standard six pin probe connector part adapted to be connected to measuring instrumentation via a cable. The cable is formed of twisted pairs of wires connected between the instrumentation and a cable connector part that mates with the probe connector part. One side of the temperature sensitive resistor, within the probe body, is connected to a common connection point of the reference and test elements. The temperature sensitive resistor is connected in common, via the cable, to the test, reference and check measurement circuits of the instrumentation so that the sensitive corrosion measurement is not affected by the presence of the large temperature sensitive resistor. Additional temperature sensitive resistance measurement and resistor energizing circuits are connected without changing the number of probe connector pins.

BRIEF DESCRIPTION OF THE DRAWINGS

FIG. 3 is a longitudinal sectional view of a bent tube or bent wire probe;

FIG. 4 is an enlarged sectional view showing the tip of the probe of FIG. 3;

DETAILED DESCRIPTION OF THE PREFERRED EMBODIMENT

Figure 1:
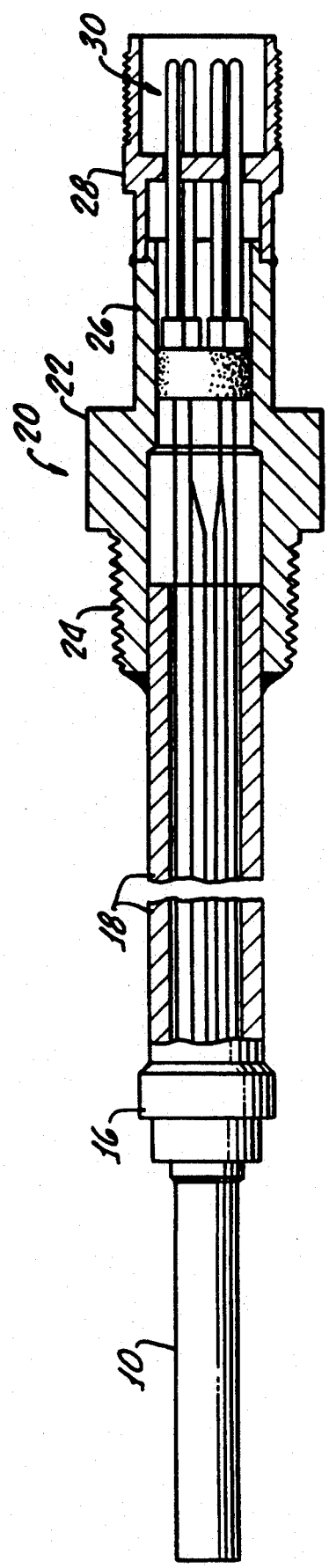
FIG. 1 is a longitudinal sectional view of a probe of concentric tubular elements.
Figure 2:
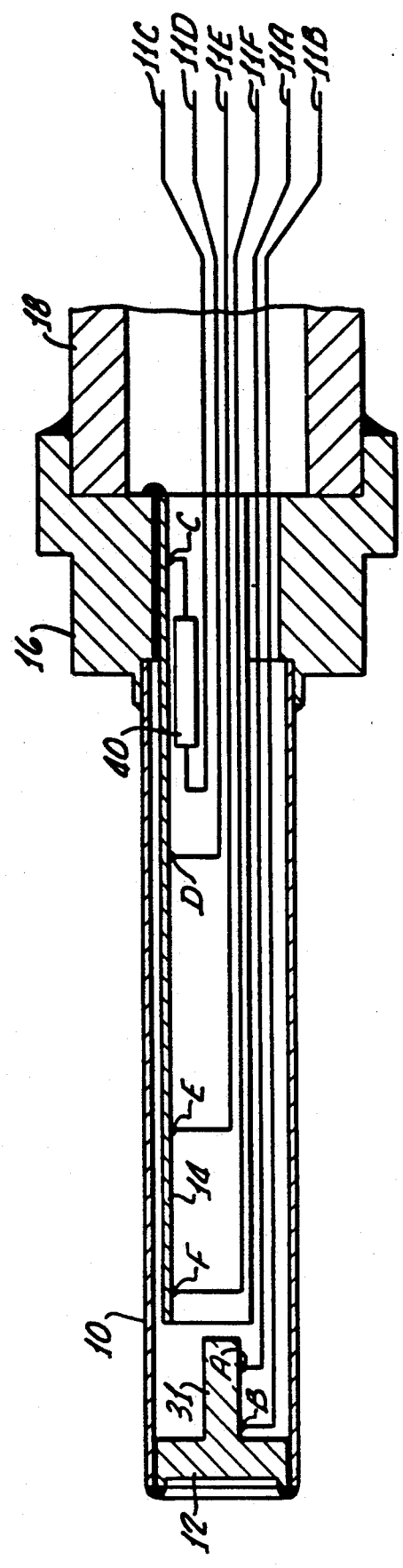
FIG. 2 is a fragmentary longitudinal enlarged view of the tip of the probe of FIG. 1.

Illustrated in FIGS. 1 and 2 is a tubular type corrosion probe of the type known as a CORROSOMETER probe manufactured by Rohrback Cosasco Systems, Inc. In this probe the test element is formed by a thin outer shell 10, having its outer end closed by a fixedly secured disc 12. An inner or reference element 14, formed from the same material as the outer shell, which may be mild steel for example, is mounted concentrically within the outer shell 10. The tubular assembly of test and reference elements has a right circular cylindrical cross section and is fixedly mounted to and partially within an end piece 16 of a tubular probe body 18. Each of the test and reference elements is fixed to the probe end piece 16, as by welding or other suitable fixed connection. The probe body 18 is mounted in a fitting 20 that may be shaped to have a tool receiving head 22 and a threaded neck 24 that is adapted to be threadedly received within a suitable female threaded fitting (not shown) formed in a wall that confines a corrosive liquid of which corrosive tendencies are to be measured. The probe fitting 20 has a fixed tubular connector section 26 terminating in a probe electrical connector part 28 in which terminate several wires (to be described below) that are connected to probe elements and extend through the tubular probe assembly and probe fitting for connection to six connector pins 30 that are fixedly mounted in the probe connector part 28. The connector pins of the probe connector part are arranged for connection to six corresponding pins of a cable connector part (not shown in FIGS. 1 and 2) which is mounted on the end of a cable that connects the probe to remote measuring and energizing instrumentation.

Illustrated in FIG. 2 are portions of the probe assembly of FIG. 1 showing the six electrical leads $11_A$, $11_B$, $11_C$, $11_D$, $11_E$ and $11_F$, all made of a conventional conductive material of the type commonly employed in instruments of this type. Leads $11_A$ and $11_F$, which are the test and reference element energizing leads, are connected respectively at a point A to an inward projection 31 fixed to disc 12 and at a point F to the outboard end of the reference element 14. Lead $11_B$ is connected at a point B to the inward projection 31, lead $11_D$ is connected at a point D to an intermediate point on the reference element 14, lead $11_E$ is connected at a point E on reference element 14 between points D and F, and lead $11_C$ is connected to a point C on the reference element that is adjacent an inboard end of the reference element.

Connected in series in the lead $11_C$ is a temperature sensitive resistor (RTD) 40 that is physically mounted (as by electrically non-conductive adhesive that fills the reference element, for example) within the tubular reference element 14 adjacent the inboard end thereof.

The probe configuration illustrated in FIGS. 1 and 2 is merely exemplary of many different types of known probe configuration (without a temperature sensitive resistor) which may be employed in practice of the present invention. Other known probe configurations include flush probes, bent wire and bent tube probes, for example. FIGS. 3 and 4 illustrate one modified physical configuration employing substantially the same electrical connections to the six leads indicated. Elements in the probe of FIGS. 3 and 4 corresponding to the probe of FIGS. 1 and 2 are designated by the same reference numerals provided with a suffix "a" to distinguish between them, but the corresponding leads $11_A$-$11_F$ are identically designated. Thus, in the probe configuration of FIG. 4 probe body 18a, having a body end piece 16a, fixedly mounts test and reference elements in the form of a small bent U-shaped solid wire or tube 10a,14a. The test element 10a is formed as first and second legs 42 and 44 of the bent tube that are adapted to be exposed to a corrosive environment. Test element leg 44 of the bent tube is continuous so as to extend through the end piece 16a into the hollow interior of probe body 18a to form the reference element 14a, which is an inward extension of the test element leg 44. Again, as in the configuration of FIGS. 1 and 2, six leads $11_A$-$11_F$ are connected to the probe elements. Leads $11_A$ and $11_F$ are connected to opposite ends of the bent wire or tubular element 10a,14a, with lead $11_A$ being connected a point A to an inboard end of the test element and lead $11_F$ being connected at point F to an inboard end of the reference element. Lead $11_B$ is connected at point B to the inboard end of the test element, positioned slightly outboard of the connection of lead $11_A$. Lead $11_D$ is connected to an intermediate point D of the reference element 14a, and lead $11_E$ is connected to the reference element 14a at point E between the connection of leads $11_D$ and $11_F$, all as illustrated in FIG. 4. Lead $11_C$ is connected to an outboard end of reference element 14a and has connected in series therein a temperature sensitive resistance device 40a that is physically mounted closely adjacent the test and reference elements within end piece 16a. As in the earlier described embodiment, the six leads are carried out through the probe body 18a to a probe electrical connector part 28a, having a set of six connector part pins 30a, which are respectively connected to individual ones of the six probe leads $11_A$-$11_F$.

Figure 5:
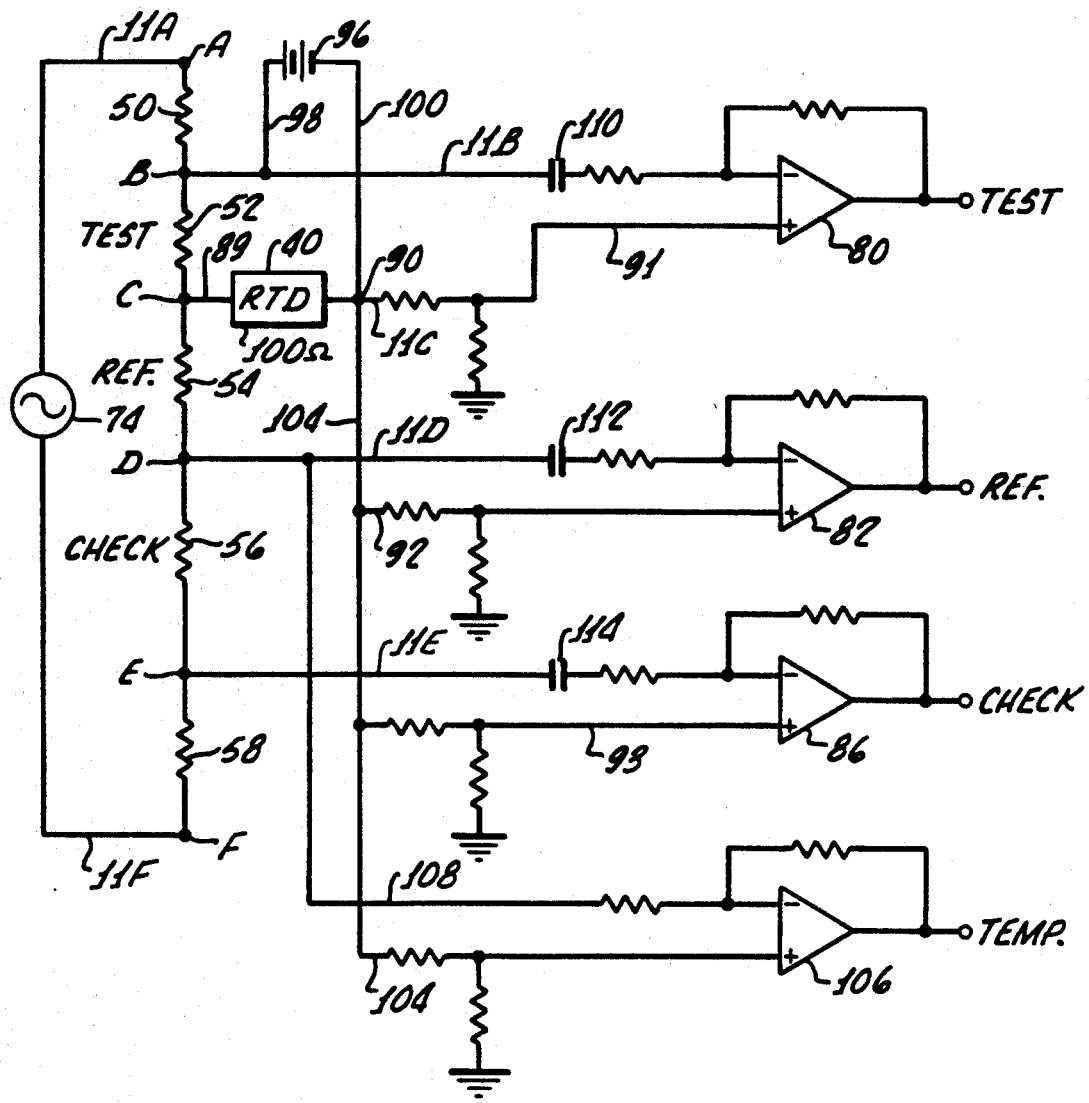
FIG. 5 is a simplified circuit diagram illustrating connections of probe elements to measuring circuits.

A simplified circuit diagram of the several probe elements is illustrated in FIG. 5, showing the various portions of the probe elements as a series of resistors 50, 52, 54, 56, and 58, all connected in series with one another and interconnected at points labeled B, C, D and E, which correspond to the similarly designated points of FIGS. 1 and 2 to which the probe wires are connected. Wires designated in FIG. 5 as $11_A$, $11_B$, $11_C$, $11_D$, $11_E$ and $11_F$ are respectively connected to the connection points A, B, C, D and E, and thus correspond with the previously described wires $11_A$-$11_F$. Wires $11_A$ and $11_F$ are connected respectively to points A and F and an AC source 74 to provide an energizing AC current that flow through the set of five series connected resistors. In the circuit of FIG. 5 resistor 52 represents the resistance of the test elements 10 and 10a, resistor 54 represents the resistance of the reference element 14 and 14a, resistor 56 represents resistance of the elements between points E and D, which is used for a check, and resistors 50 and 58 represent resistance of the elements between the points B and E and points A and F respectively to which the energizing signal is applied. For corrosion measurement, voltage across the test element 52 (which is proportional to its resistance) is measured by means of a test differential or operational amplifier 80 which has its inverting and noninverting inputs connected respectively to point B at one end of test element 52 and to point C at the other end of test element 52. Voltage across the reference element 54 (also directly proportional to resistance) is measured by a second operational amplifier 82 which has its inputs connected respectively to point D at the end of reference element 54 and to point C which is the junction or common connection between test and reference elements 52 and 54. In this discussion the presence of the RTD 40 is temporarily ignored. Outputs of the test and reference amplifiers 80 and 82 are fed to other circuitry (not shown) which calculates a ratio between the two measured voltages to define a corrosion signal. Because test element 52 is exposed to the corrosive environment, it is subject to corrosion or erosion, which decreases its cross-sectional area, thereby increasing its resistance. The reference resistance 54 is protected from the environment, and thus does not change with resistance. However, because both resistors change with temperature, the use of the reference resistor to provide a ratio of resistances accomplishes compensation for relatively long term temperature variation of the test resistance element.

For purposes of checking the measurement, the check resistor 56 is provided. This resistor, also protected from the environment, has a resistance that is a known relation, such as 1/5th, to the resistance of the reference resistor 54. Thus the ratio of resistance of reference resistor 54 to the ratio of combined resistances of reference and check resistors 54 and 56 is predetermined to be 0.8. This reading should remain fixed and is used as a check on the operation of the instrumentation.

A check operational amplifier 86 has its inverting and noninverting inputs connected respectively to point E at the junction of resistors 56 and 58 and to point C, the common connection point.

It will be seen that point C, the common connection between test and reference elements 52 and 54, is connected to one input of each of the test, reference and check amplifiers 80, 82 and 86.

The temperature sensitive resistor 40, which may be a common commercially available platinum temperature sensitive resistor, having either one lead on one end and one on the other, or two leads on each end for the purpose of compensating for lead resistance of the resistor, is connected in series in the common input of each of the measuring amplifiers 80, 82 and 86. Thus one end 89 of the temperature sensitive resistor 40 is connected to the common connection point C between the test element 52 and reference element 54. The other end 90 of the temperature sensitive resistor is connected in common to each of the leads $11_C$, $11_D$, and lead $11_E$ that are connected to the noninverting inputs of respective test, reference and check amplifiers 80, 82 and 86 by leads 91, 92 and 93, respectively.

To read the resistance of temperature sensitive resistor 40 a source 96 of DC current is connected via a line 98 to point B and thence through the very small (compared to the resistance of the temperature sensitive resistor 40) resistance of test element 52 to end 89 of the temperature sensitive resistor. The other end 90 of the temperature sensitive resistor is connected to the source 96 via a lead 100. To measure voltage across the temperature sensitive resistor, and thus enable measurement of its resistance, point 90 at one end of the resistor is connected via a line 104 to the noninverting input of a temperature measuring differential amplifier circuit 106. The inverting input of amplifier 106 is connected via a lead 108 to the lead $11_D$ which connects to point D at the end of reference resistor 54. Again the presence of the very small resistance of resistor 54 in this measuring circuit has negligible effect on the measured resistance of the temperature sensitive resistor 54 because the latter, as previously mentioned, has a value in the order of one hundred thousand times greater than the resistance of reference element 54.

The above described connections are the same for either the probe of configuration shown in FIGS. 1 and 2 or of the configuration shown in FIGS. 3 and 4. Further, the circuit arrangement may be readily applied to other probes of other physical configurations.

It is noted that the corrosion measurement is fundamentally achieved by measuring in test amplifier 80 the resistance of test element 52 and by measuring in reference amplifier 82 the resistance of the reference element 54. The ratio of these resistances provides an indication of the measured corrosion compensated for temperature, as previously mentioned. The presence of the very large resistance of temperature sensitive resistor 40 in the measuring circuits has no effect on the measurement of the ratio of the test and references resistances because the temperature sensitive resistor is connected in the same manner in series with the noninverting input of each of the test and reference amplifiers. Thus the effect of the very large resistance of the temperature sensitive resistor 40 is the same on both amplifiers to provide equal gain in measuring the ratio of the outputs of the two. Similarly, in providing the check measurement, which determines the ratio between the outputs of the reference and check amplifiers, the temperature sensitive resistor is connected in the same manner between the common connection point C and each of the noninverting inputs of the reference and check amplifiers so that its effect on the check measurement is eliminated.

The DC current drive for the temperature sensitive resistor and the DC measuring circuit 106 for measurement of resistance are effectively isolated from the AC current drives and the AC measuring circuits for the corrosion elements by the use of conventional circuit components, such as, for example, DC blocking capacitors 110, 112 and 114 connected in the input circuits of the test, reference and check amplifiers 80, 82 and 86.

It will be noted that only by placing the temperature sensitive resistance 40 in series and in common in all of the common leads to the test, reference and check amplifiers can the otherwise adverse effects of the very large resistance of the temperature measuring device be eliminated from the very sensitive measurement of the milli ohm resistances of the corrosion measuring elements. Location of the temperature sensitive resistance in any of the other lines would destroy the corrosion measurement. Nevertheless, with the illustrated arrangement, the probe measures both temperature and corrosion, and yet it does so without any significant change in wiring configuration and without any change in the standard six pin probe connector part.

Figure 6:
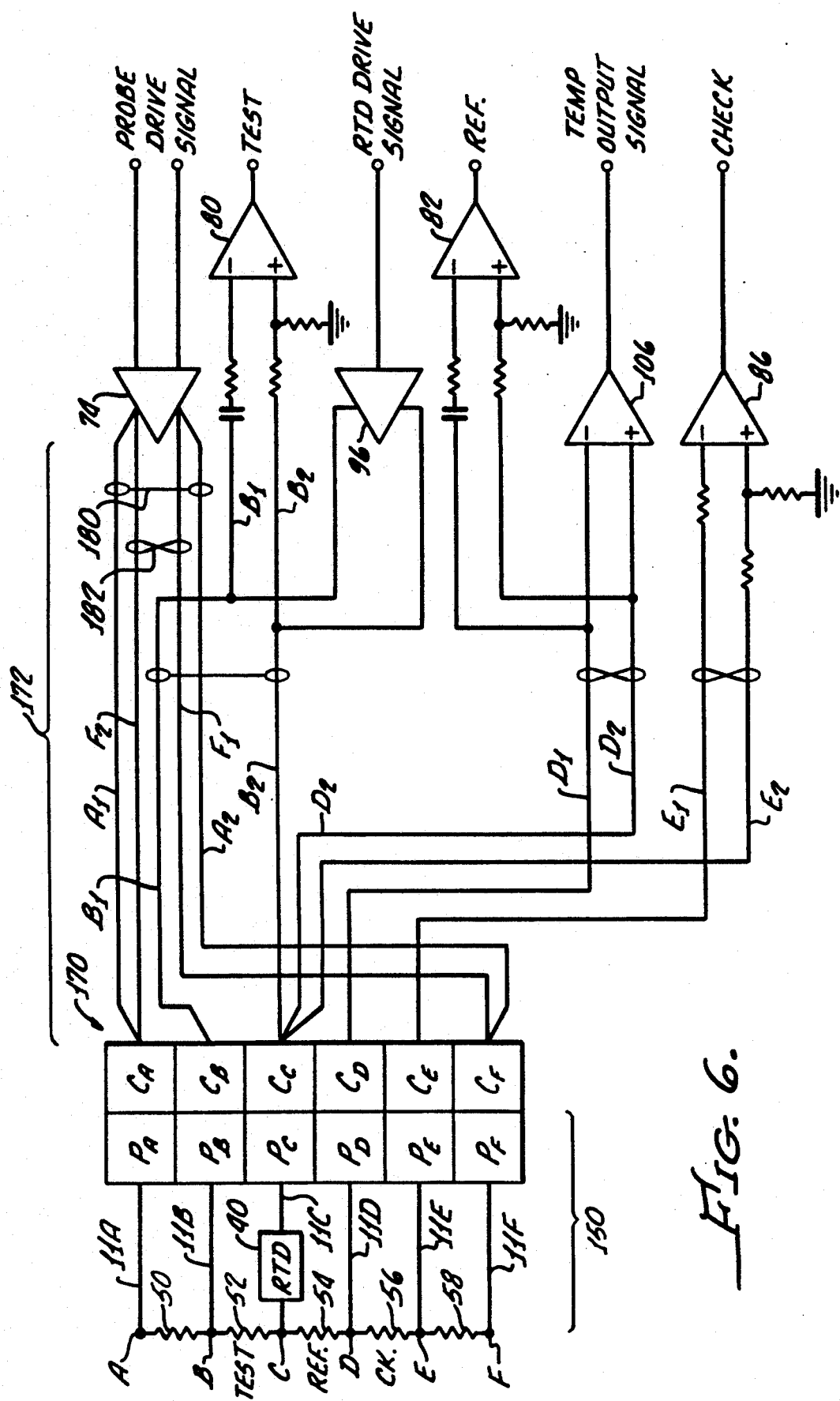
FIG. 6 schematically illustrates the connection of five twisted pairs of wires to the six pin cable connector part.

The manner in which wires of the probe cable are connected to the standard cable connector part so as to enable the electrical connections of components as illustrated in FIG. 5 is shown in FIG. 6, which comprises a simplified illustration of the instrumentation, the probe and its connector part, and the cable and its cable connector part that are interconnected between the test probe and the instrumentation. As shown in FIG. 6, the probe with its connector part is generally indicated by reference numeral 150. The probe includes the probe measuring elements, including test, reference and check elements, and the temperature sensitive resistance 40, configured and arranged as previously described. The several probe elements are connected by single wire leads $11_A$, $11_B$, $11_C$, $11_D$, $11_E$ and $11_F$ to probe connector part pins designated as $P_A$, $P_B$, $P_C$, $P_D$, $P_E$, and $P_F$, respectively. The six probe connector part pins are detachably coupled to a cable connector part 170, including cable connector part pins $C_A$, $C_B$, $C_C$, $C_D$, $C_E$, and $C_F$, respectively.

FIG. 6 illustrates the cable connector part, generally designated as 170, connected by a cable, generally designated as 172, to the measuring instrumentation at the remote end of the cable and including test amplifier 80, reference amplifier 82, check amplifier 86, temperature measuring amplifier 106, corrosion probe drive current source 74, and the temperature sensitive resistance DC drive 96. The cable 172 that connects the instrument to the cable connector part 170 is composed of ten individual wires provided as five twisted pairs. Twisted pairs are employed for eliminating cross-talk between the several wires, which is particularly important in the light of the very small signals that are involved in the corrosion measurement. In the conventions employed herein in FIG. 6 wires of one pair are shown in the drawing as being connected by a symbolic line that interconnects a symbolic loop around each of the wires of the pair. Thus, for example, individual wires designated as $A_1$ and $A_2$ in FIG. 6 are shown interconnected by a symbolic line 180 to indicate that wires $A_1$ and $A_2$ form a single twisted pair. Similarly, $F_1$ and $F_2$ are connected by a symbolic line 182, which indicates that single wires $F_1$ and $F_2$ form a single twisted pair.

For energization of the probe, one side of the probe drive signal from source 74 is coupled to a first wire $A_1$ of a first twisted pair and a second wire $F_2$ of a second twisted pair. Both of these are connected to the cable connector part pin $C_A$. Effectively then this is the electrical connection to terminal A (pin $P_A$) of the probe. For the other side of the energization of the probe, the other side of the source 74 is connected to both the second lead $F_1$ of the twisted pair $F_1$, $F_2$ and to the second lead $A_2$ of the twisted pair $A_1$, $A_2$, with both wires $F_1$ and $A_2$ being connected to cable connector part pin $C_F$. Thus, power is provided to the probe through two wires to pins $C_A$ and $P_A$ and through two wires to pins $P_F$ and $C_F$.

A twisted pair $B_1$, $B_2$ has the individual wires thereof connected respectively to the inverting and noninverting inputs of the test amplifier 80, with wire $B_1$ being connected at its remote end to pin $C_B$ of the cable connector part and wire $B_2$ being connected at its remote end to the common cable connector part pin $C_C$. Wires of this same pair of wires $B_1$, $B_2$ are also connected to the output of the temperature sensitive resistor driver or current source 96.

For measurement of resistance of the corrosion reference element, wires $D_1$ and $D_2$ of a twisted pair are connected at the instrument to the inverting and noninverting inputs respectively of reference measuring amplifier 82, with wire $D_1$ of this pair being connected at its remote end to pin $C_D$ of the cable connector part, and the second wire $D_2$ of this pair being connected to the common pin $C_C$ of the cable connector part. The wires $D_1$ and $D_2$ of this pair are also connected to the temperature measuring amplifier 106, being connected respectively to its inverting and noninverting input.

Check amplifier 86 is connected by the wires $E_1$, $E_2$ of a twisted pair to respective pins $C_E$ and the common pin $C_C$ of the cable connector part 170.

Of course, in the probe to cable connector the two connector parts are connected so that pin $P_A$ connects to pin $C_A$, pin $P_B$ connects to $C_B$, etc. The connections of the probe connector parts to the probe itself are as previously described and as generally illustrated in FIG. 6. Accordingly, the arrangement enables the use of standard six pin connectors. The common connecting point C between test and reference resistors 52,54, is connected with its temperature sensitive resistance 40 in series with all of the three individual wires $B_2$, $D_2$, $E_2$ of three different twisted pairs of the cable. Each of these wires $B_2$, $D_2$, $E_2$ is connected for corrosion measurement to the common input of the test, reference and check amplifiers, respectively, and thus accomplish elimination of the adverse effects of the presence of the large temperature sensitive resistor.

It will be noted that by using DC drive and DC coupled measuring circuitry for the temperature sensitive resistance and AC drive and AC coupled measuring circuitry for the corrosion measurement both measurements may be carried out simultaneously without interference. Moreover, merely by connecting the temperature sensitive resistor as indicated and providing temperature sensitive resistor drive and temperature sensitive resistor measurement connections, as illustrated in FIG. 6, a standard six pin connection and a standard cable employing five twisted pairs is still capable of use in the modified probe which is now capable of measurement of both corrosion and instantaneous temperature, without change to its standard connector pin or cable configuration.

The foregoing detailed description is to be clearly understood as given by way of illustration and example only, the spirit and scope of this invention being limited solely by the appended claims.

What is claimed is:

1. An electrical resistance corrosion and temperature probe comprising:
   a resistance test element adapted to be exposed to an environment of which corrosive characteristics are to be measured and having a test connection point,
   a resistance reference element protected from said environment and having a reference connection point and connected to said test element at a common connection point,
   a measuring circuit having first and second inputs respectively connected to said test and reference points and having a common input, and
   a temperature sensitive device connected between said common input and said common point, said temperature sensitive device being adapted to measure temperature at said probe.

2. The probe of claim 1 wherein said circuit comprises a first amplifier having inputs connected to said test point and to said temperature sensitive device, and a second amplifier having inputs connected to said reference point and to said temperature sensitive device.

3. The probe of claim 1 wherein said test and reference elements have first and second resistances that are measured by said circuit and wherein said temperature sensitive device has a resistance that is many thousand times greater than said first and second resistances.

4. The probe of claim 2 including a third amplifier having inputs connected to said temperature sensitive device and to one of said test and reference points.

5. An electrical resistance corrosion and temperature measuring probe comprising:
   test and reference elements connected to each other at a junction, said test element comprising a resistance test element adapted to be exposed to an environment of which corrosive characteristics are to be measured, said reference element being protected from said environment,
   test and reference leads connected respectively to said elements and a common lead connected to said junction, and
   a temperature sensitive resistor connected in said common lead, said temperature sensitive resistor being adapted to measure temperature at said probe.

6. The probe of claim 5 wherein said test and reference elements have resistances to be measured, and wherein said temperature sensitive resistor has a resistance many times greater than the resistances of said test and reference elements.

7. The probe of claim 5 including means for exciting said temperature sensitive resistor comprising a current generating circuit connected to said common lead and one of said test and reference leads, and means for measuring resistance of said resistor.

8. The probe of claim 7 wherein said means for measuring comprises a measuring circuit connected to said common lead and to the other of said test and reference leads.

9. A corrosion and temperature measuring instrument comprising:
   a resistance test element adapted to be exposed to an environment of which corrosive characteristics are to be measured,
   a resistance reference element protected from said environment and mounted adjacent to and connected to said test element,
   resistance responsive means responsive to said test and reference elements for generating test and reference signals indicative of corrosion experienced by said test element, said means for generating test and reference signals comprising:
   first and second leads having said test element connected therebetween,
   a third lead, said reference element being connected between said second and third leads, and
   test and reference measuring circuits having inputs connected to said leads, and
   a temperature sensitive resistor mounted adjacent said test and reference elements and connected in said second lead, and
   means for measuring resistance of said resistor, said temperature sensitive resistor having a resistance that is a measure of temperature at said probe.

10. The instrument of claim 9 wherein said means for generating test and reference signals comprise a first measuring circuit connected to said resistor and to one of said first and third leads, and a second measuring circuit connected to said resistor and to the other of said first and third leads.

11. The instrument of claim 9 wherein said means for measuring comprise means connected with said second lead and one of said first and third leads for flowing current through said resistor.

12. The instrument of claim 10 wherein said means for measuring comprise a measuring circuit connected to said resistor and one of said first and third leads, and including a resistor energizing circuit connected to said resistor and the other of said first and third leads.

13. A combined temperature and electrical resistance corrosion measuring instrument comprising:
   a test element adapted to be exposed to an environment of which corrosive characteristics are to be measured and having a test resistance,
   a reference element mounted adjacent said test element and protected from corrosion by said environment and having a reference resistance, said reference element being connected to said test element at a common point, a first measuring circuit connected between a point on said test element and said common point for measuring resistance of said test element, a second measuring circuit connected between a point on said reference element and said common point for measuring resistance of said reference element, a temperature sensitive resistor having a first end connected to said common point and having a second end, and a third measuring circuit connected to said second end of said temperature sensitive resistor and to one of said test and reference elements for measuring resistance of said temperature sensitive resistor.

14. The measuring instrument of claim 13 wherein said temperature sensitive resistor is connected between said common point and each of said first and second measuring circuits.

15. The measuring instrument of claim 13 including means connected between the second end of said temperature sensitive resistor and the other one of said test and reference elements for flowing current through said temperature sensitive resistor.

16. The measuring instrument of claim 13 including means for transmitting an energizing alternating current through said test and reference elements, and means for transmitting an energizing direct current through said temperature sensitive resistor.

17. The measuring instrument of claim 13 wherein said test element comprises an elongated hollow tubular member, and wherein said reference element comprises an elongated hollow tubular member within said test element.

18. The measuring instrument of claim 17 wherein said temperature sensitive resistor is mounted within said reference element.

19. The measuring instrument of claim 13 wherein said temperature sensitive resistor is mounted adjacent said test and reference elements.

20. The measuring instrument of claim 13 including a probe body, and a loop of electrically conductive material extending outwardly from said probe body, said loop having a first section that is positioned outside of said body for defining said test element and having a second section positioned wholly within said body for defining said reference element, said temperature sensitive resistor being mounted within said body adjacent said reference element.

21. The measuring instrument of claim 17 wherein said temperature sensitive resistor is mounted within said hollow tubular member.

22. The measuring instrument of claim 13 wherein said test element has a test connection point and said reference element has a reference connection point, said first measuring circuit being connected between said common point and said test connection point, and said second measuring circuit being connected between said reference connection point and said common point.

23. The measuring instrument of claim 22 including a direct current source having a first connection to one end of said temperature sensitive resistor and having a second connection to one of said test and reference connection points.

24. The measuring instrument of claim 23 wherein said third measuring circuit has a first connection to said one end of said temperature sensitive resistor and a second connection to the other of said test and reference connection points.

25. The measuring instrument of claim 13 including a cable interconnecting said test and reference element points and said common point with said measuring circuits, said cable comprising first and second twisted pairs of wires, said first pair having a first wire connected to said test element point and having a second wire connected to said common point, said second pair having a first wire connected to said reference element point and a second wire connected to said common point, the wires of one of said first and second pairs being connected to said third measuring circuit.

26. The measuring instrument of claim 25 including a temperature sensitive resistor energizing circuit, and wherein the wires of the other of said first and second pairs are connected to said temperature sensitive resistor energizing circuit.

27. The measuring instrument of claim 13 including a probe connector part having no more than six pins connected to said reference and test elements and to said resistor, and a multi-wire cable connected to said measuring circuits and having a cable connector part with no more than six pins configured and arranged to be connected to corresponding pins of said probe connector part.

28. The measuring instrument of claim 27 wherein said cable includes five twisted pairs of wires connected to said six pins of said cable connector part.

* * * * *